(12) United States Patent
Schwenke et al.

(10) Patent No.: US 7,001,393 B2
(45) Date of Patent: Feb. 21, 2006

(54) SERVO-CONTROLLED IMPACTING DEVICE FOR ORTHOPEDIC IMPLANTS

(75) Inventors: Thorsten Schwenke, Chicago, IL (US); Markus A. Wimmer, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 10/984,497

(22) Filed: Nov. 9, 2004

(65) Prior Publication Data

US 2005/0101962 A1    May 12, 2005

Related U.S. Application Data

(60) Provisional application No. 60/518,752, filed on Nov. 10, 2003.

(51) Int. Cl.
*A61F 5/00*        (2006.01)
(52) U.S. Cl. ....................................... 606/86
(58) Field of Classification Search ................. 606/86, 606/99, 100
See application file for complete search history.

(56) References Cited

U.S. PATENT DOCUMENTS

2004/0106916 A1 *  6/2004  Quaid et al. ................... 606/1

OTHER PUBLICATIONS

"Chondrocyte damage following osteochondral grafting using metal and plastic punhces: comparative study in an animal model", *Journal of Orthopedic Surgery 2002: 10(22):170-172.*

"Inadequate placement of osteochondral plugs may induce abnor stress-stain distributions in articular cartilage—finite element simulations", by Wu JZ, Herzog W., Hasler EM, http://www.ncbi.nim.nih.gov, printed on Sep. 24, 2004.

\* cited by examiner

*Primary Examiner*—Eduardo C. Robert
*Assistant Examiner*—Michael J. Araj
(74) *Attorney, Agent, or Firm*—Foley & Lardner LLP

(57)    ABSTRACT

A servo-controlled impacting device for orthopedic implants includes one or more sensors, an impacting device, and a controller with an interface. The controller is configured to provide control signals to an impactor in response to feedback signals from at least one sensor proximate an orthopedic implant subject to a force applied by the impactor. The interface is coupled to the controller and is configured to enable parameters to be set related to the operation of the controller.

18 Claims, 4 Drawing Sheets

SERVO-CONTROLLED IMPACTING DEVICE FOR ORTHOPEDIC IMPLANTS

FIELD OF THE INVENTION

The present invention relates generally to the field of orthopedic implants. More particularly, the present invention relates to a servo-controlled impacting device for orthopedic implants.

BACKGROUND OF THE INVENTION

Currently, over 250,000 primary total hip arthroplasties (THA) are performed each year in the United States alone. The number of revision surgeries is also increasing. Constant improvements in implant design, materials, and surgery techniques help the patient regain a normal lifestyle ever sooner, together with a more promising outlook on long-term success. One recent technological breakthrough in THA is the Minimal Invasive Surgery (MIS) technique for artificial hip joints, which cuts down hospitalization time significantly. With MIS, patients may start ambulating within 24 hours after surgery.

One important goal of THA is to assure sufficient primary stability, guarantee bone ingrowths, and achieve long-term success. Good primary stability can be reached through press-fit of the implant-bone interface. Conventionally, an optimal relationship requires the right tools along with surgeon's experience. As such, proper training and continuous technical improvement help to meet the increasing demand of fully functioning hip replacements.

Total hip displacement surgeries generally consist of different phases, from pre-operative measurements to exposing the proximal femur and performing the osteotomy of the femoral neck. After opening the femoral canal and rasping to the appropriate size, a trial and then the final implant are inserted into the proximal femur. The femoral stem of the final implant is pressed down the femoral canal by hand until it stops, usually 2 to 3 cm above the neck osteotomy. The implant is then tapped with an impactor until its final position is reached, and ideally the implant stops advancing. The right amount of tapping force has to be applied to gain a good press-fit situation of the implant, while the insertion resistance of the implant may increase as the stem is advanced down the canal.

Obtaining the optimal press-fit under the given conditions and, thus, good primary stability often depends on the surgeon's experience. Implant size, rasping technique, bone constitution, and tapping strength are leading factors influencing the outcome of the hip arthroplasty.

If the femoral stem is inserted outside an ideal press-fit bandwidth, it is either too loose and, therefore, lacks primary stability, or too tight, leading to stress concentration and, in extreme cases, fracture of the femur. Advanced surgery techniques, such as MIS, are subject to constraints like limited access to the femoral neck and reduced visibility and acoustical feedback, which increase the risk for effects of sub-ideal implant insertion. Sub-optimal primary stability and fracture of the femur may necessitate bigger incisions and thus contradict the advantages of MIS. New tools need to be developed to overcome these and other limitations of conventional orthopedic implants and to guarantee continuous high quality THA's.

Conditions of osteoarthritis can be affected by cartilage defects. The transplantation of osteochondral (cartilage-bone) plugs is an alternative approach to treat local, full thickness cartilage defects in young patients. The process involves grafting a plug from the patient or a donor and placing it into a predrilled hole in the patient's body. Plug placement is generally conducted with a metal or plastic punch or hammer. During this process, it is difficult to control the amount of the press fit tolerance and the position of the osteochondral plug in the recipient hole.

Inadequate placement of osteochondral plugs may produce abnormal stress and strain distributions within the cartilage, and thus influence the regeneration of the injured cartilage site and the maintenance of opposing, healthy cartilage surfaces. Further, if too much force is used when pounding in the osteochondral plug, cell viability may be adversely affected and stimulation inhibited. Hence, there is a need for tools to better control osteochondral plug impaction and placement during osteochondral plug transplantation. Further, there is a need for tools which can utilize sensors and a feedback loop to determine the proper amount of force to ensure optimal osteochondral plug transplantation.

SUMMARY OF THE INVENTION

In accordance with an exemplary embodiment, a servo-controlled impacting device for orthopedic implants includes a controller and an interface. The controller is configured to provide control signals to an impactor in response to feedback signals from at least one sensor proximate an orthopedic implant subject to a force applied by the impactor. The interface is coupled to the controller and is configured to enable parameters to be set related to the operation of the controller.

Another exemplary embodiment relates to a surgical device including an orthopedic implant impactor and a controller. The orthopedic implant impactor is configured to impact an orthopedic implant with sufficient force to insert the orthopedic implant. The controller communicates control signals to the orthopedic implant impactor. The control signals are based on pre-programmed data and feedback signals received from one or more sensors.

Another exemplary embodiment relates to an impacting device for orthopedic implant surgery. The device includes means for impacting an orthopedic implant to insert the orthopedic implant in a bone, means for sensing conditions of the implanting, means for determining control signals based on pre-programmed references and sensed conditions, and means for communicating the determined control signals to adjust force applied by the impacting means.

Another exemplary embodiment relates to a sensing apparatus having a set of sensors. The set of sensors detect conditions associated with an orthopedic implant surgery and direct feedback signals regarding these conditions to a controller.

Yet another exemplary embodiment relates to an impacting device for use in osteochondral plug transplantation. The device includes means for impacting a grafted osteochondral plug to insert the osteochondral plug into a predrilled hole in a patient's body. The device further includes means for sensing conditions of the impacting, means for determining control signals based on pre-programmed references and sensed conditions, and means for communicating the determined control signals to adjust force applied by the impacting means.

Further objects, features and advantages of the invention will be apparent from the following detailed description when taken in conjunction with the accompanying drawings.

DETAILED DESCRIPTION OF THE INVENTION

Figure 1:
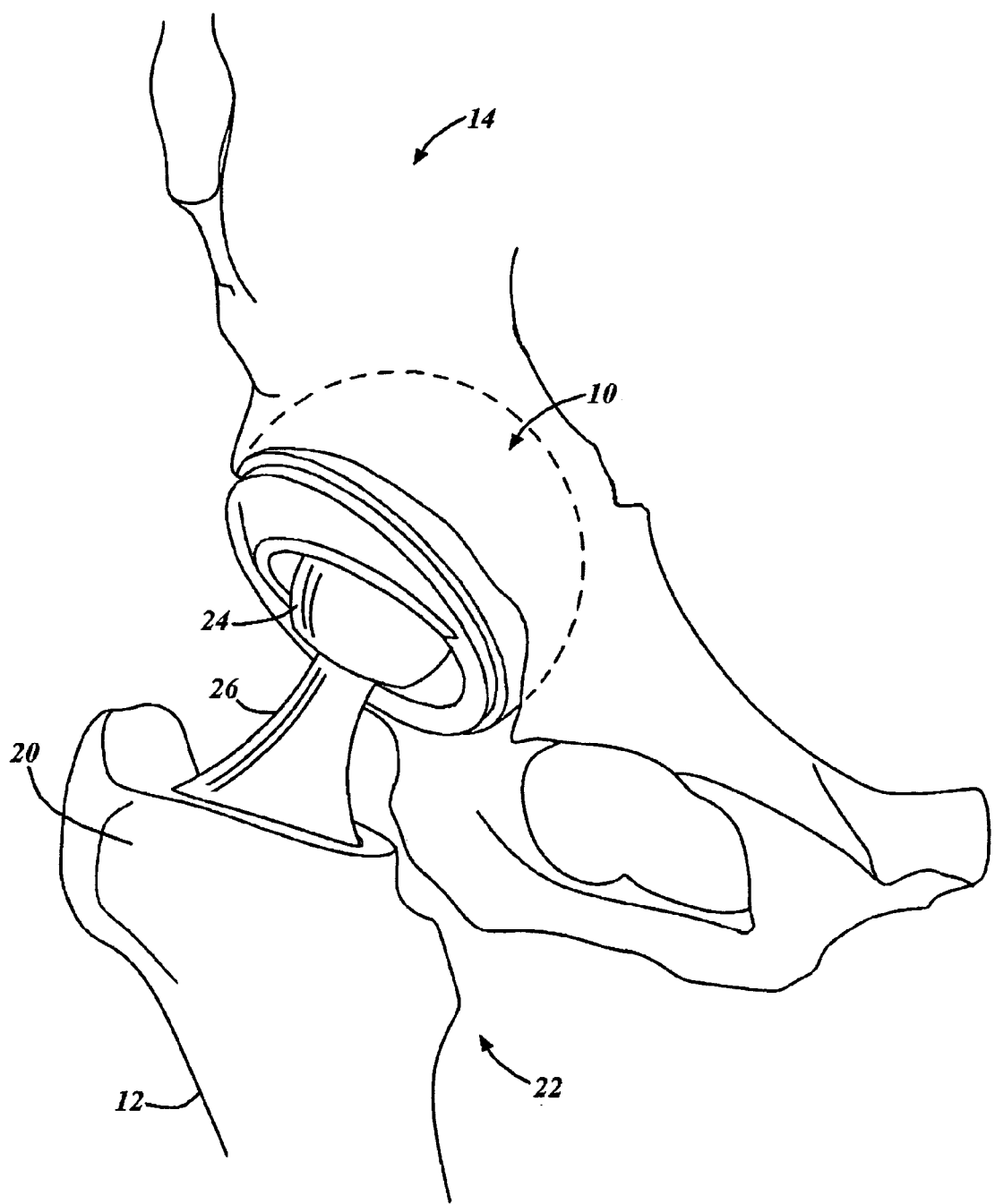
FIG. 1 is a diagrammatic representation of an anterior cross-sectional view of an example human hip having a femoral implant.

FIG. 1 illustrates an anterior cross-sectional view of an example human hip having a femoral implant. The semi-circular shape of the acetabulum 10 can be seen. The upper leg bone, or femur 12, which can be seen just below the ilium 14, is the longest and strongest bone in the body. The upper end of the femur 12 is provided with a spheroidally shaped head, a neck, a greater trochanter 20, and a lesser trochanter 22.

Total hip replacement typically involves a complete internal dissection of the hip joint. The conventional surgical procedure used during total hip replacement involves making a surgical incision to provide an approach to the hip. Once the hip is exposed, the joint is dislocated so that the femoral head 16 and acetabular socket 10 can be accessed. The femoral head and neck are then dissected. Once the femoral head and neck have been removed, the femoral canal (the central core of the bone) is reamed so as to provide a cavity into which a femoral implant may be inserted. The implant includes a spheroidally-shaped head 24 and a neck 26.

Figure 2:
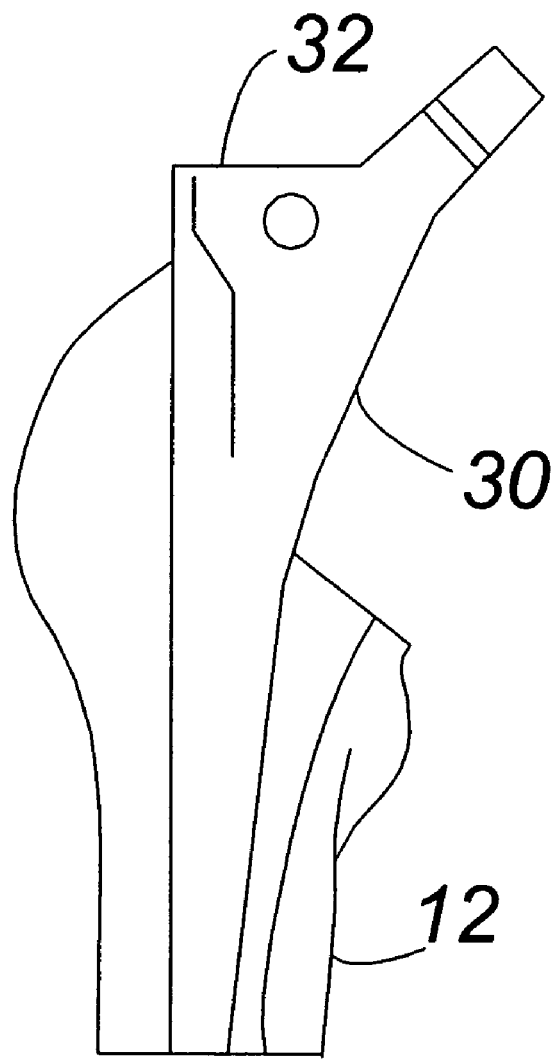
FIG. 2 is a diagrammatic representation of an example implant being positioned in a femoral canal.

FIG. 2 illustrates a cross-sectional view of an example implant 30 being positioned in a femoral canal. A surgeon generally uses hand pressure at first and then a mallet. Good press-fit is achieved through impaction of cancellous bone along the proximal part of the implants.

The force applied to the implant 30 is important throughout the implanting process. Excessive force can result in bone cracking while too little force may not allow the implant 30 to provide sufficiently primary stability. When the implant 30 is placed in too tight a fit, microcracks can occur. However, loose fit implants can move, which is also deleterious for bone growth.

Figure 3:
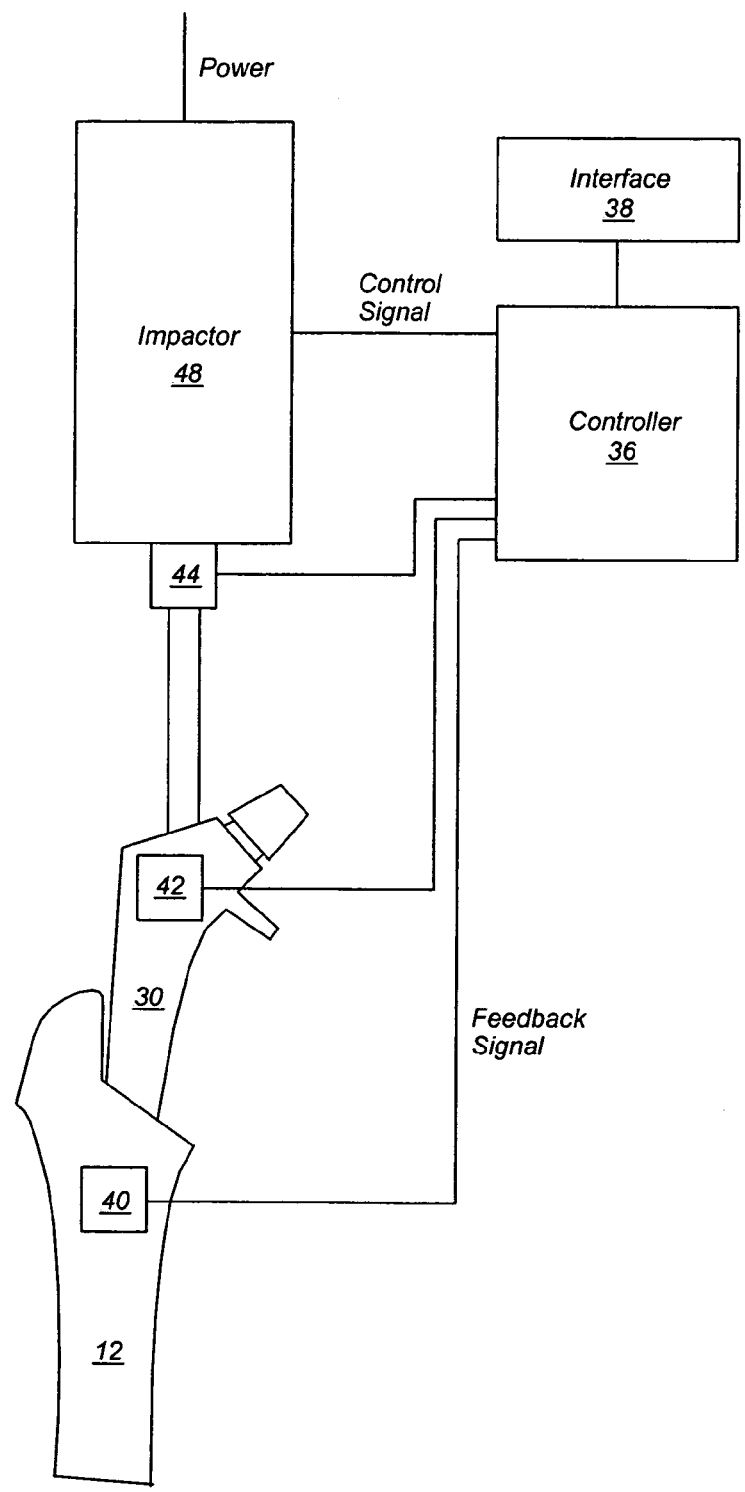
FIG. 3 is a schematic representation of a servo-controlled impacting device for orthopedic implants in accordance with an exemplary embodiment.

FIG. 3 illustrates a servo-controlled impacting device for orthopedic implants. The device includes a controller 36 having an interface 38. The device is considered servo-controlled because it receives and processes feedback signals and provides an electrical input control signal to an impacting device that is driven with a force generated with separate power. The controller 36 receives feedback signals from at least one of sensors 40, 42, and 44. Sensor 40 is located proximate the femur 12, sensor 42 is located proximate the implant 30, and sensor 44 is located proximate an impactor 48. The sensors may be located in different positions. The controller 36 provides control signals to the impactor 48 that adjust the force applied by the impactor 48 to insert the implant 30 into the femur 12. The impactor 48 can be a user-directed impactor or a powered impactor.

Impacting force from the impactor 48 can depend on several input parameters, such as implant shape and surface properties, bone quality, resistance due to insertion progression, and the desired press-fit result. Signals from the sensors 40, 42, and 44 can be force, pressure, or acceleration signals. The sensors 40, 42, and 44 can also include vibrational sensors that indicate proper seating of the implant. In at least one embodiment, the controller 36 determines what control signals to send the impactor 48 based on the feedback signals from the sensors 40, 42, and 44, pre-programmed profiles, bone and implant conditions, and the actual insertion situation. The force and frequency of the impactor action 48 can both be controlled.

The impactor 48 can be pneumatically or electrically driven, and is handheld by the surgeon. The interface 38 allows the user to set parameters, such as insertion force. The interface 38 can include a display that provides graphical or numerical feedback on key parameters, limit detection, and other information. As such, the impacting force onto the femoral shaft during implant insertion can be more accurately applied, such that an optimal press-fit of the hip implant shaft can be obtained. Alternatively, the impactor 48 can be hand-driven. In the hand-driven embodiment, an acoustic or visual signal can be provided when a prosthesis fits too tight or too much force or too high a frequency is applied.

Figure 4:
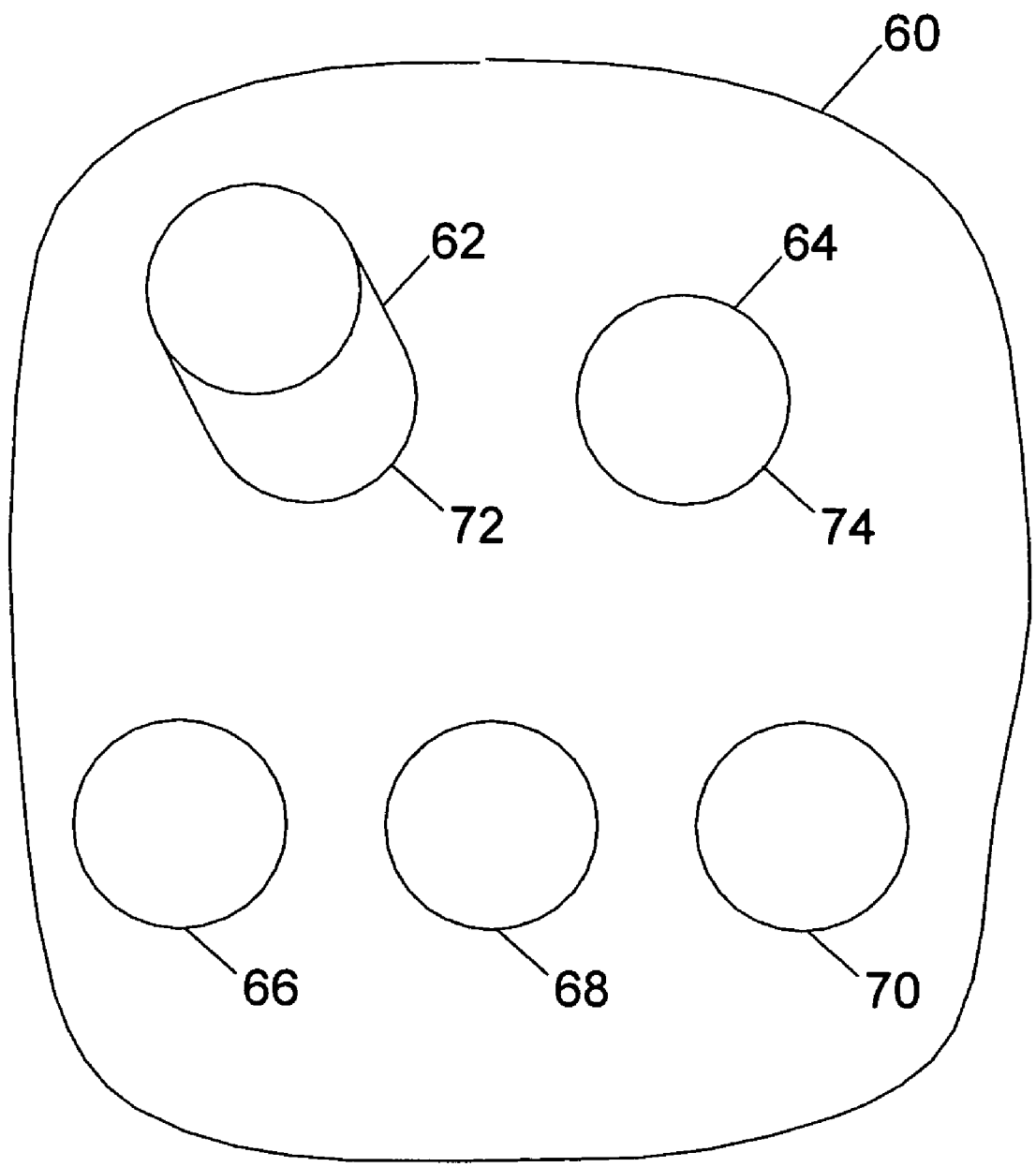
FIG. 4 is a diagrammatic representation of a mosaic plastic performed on the surface of a femoral condyle.

FIG. 4 illustrates an osteochondral plug transplant on a femoral condyle 60. A surgeon first pre-drills holes 66, 68, 70, 72 and 74 into a patient's femoral condyle 60. A grafted osteochondral plug 62 is placed into pre-drilled hole 72. When placing an osteochondral plug 62, the amount of force applied is important in determining the success of the operation. Sufficient force must be applied to properly position the osteochondral plug 62 such that abnormal stress and strain distributions are avoided. However, excessive force or improper placement may lead to reduced cell viability and negatively influence the regeneration of the injured cartilage site.

A properly positioned osteochondral plug 64 is flush with the surface of the femoral condyle 60. Proper positioning is difficult to achieve given that surgeons generally pound an osteochondral plug 62 in with a mallet or hammer. The servo-controlled impactor described with reference to FIG. 3 allows the force applied to an osteochondral plug to be controlled to a much greater degree. In one embodiment, sensors, which may be placed on the femoral condyle 60, the osteochondral plug 62, the impactor 48, or elsewhere, may be used by the controller 36 to help determine the force and frequency required by the impactor 48.

It should be understood that the invention is not limited to the embodiments set forth herein as illustrative, but embraces all such forms thereof as come within the scope of the following claims. For example, any of a variety of different implants can be used, not just hip implant and osteochondral plugs.

What is claimed is:

1. A servo-controlled impacting device for orthopedic implants, the device comprising:

a controller configured to provide control signals to an impactor in response to feedback signals from at least one sensor proximate an orthopedic implant subject to a force applied by the impactor; and an interface coupled to the controller and configured to enable parameters to be set related to the operation of the controller;

wherein the at least one sensor comprises a sensor on the orthopedic implant.

2. A servo-controlled impacting device for orthopedic implants, the device comprising:

a controller configured to provide control signals to an impactor in response to feedback signals from at least one sensor proximate an orthopedic implant subject to a force applied by the impactor; and an interface coupled to the controller and configured to enable parameters to be set related to the operation of the controller;

wherein the at least one sensor comprises a vibrational sensor.

3. A servo-controlled impacting device for orthopedic implants, the device comprising:

a controller configured to provide control signals to an impactor in response to feedback signals from at least one sensor proximate an orthopedic implant subject to a force applied by the impactor; and an interface coupled to the controller and configured to enable parameters to be set related to the operation of the controller;

wherein the feedback signals comprise force, pressure, or acceleration signals.

4. A servo-controlled impacting device for orthopedic implants, the device comprising:

a controller configured to provide control signals to an impactor in response to feedback signals from at least one sensor proximate an orthopedic implant subject to a force applied by the impactor; and an interface coupled to the controller and configured to enable parameters to be set related to the operation of the controller;

wherein the parameters comprise implant shape and properties, bone condition, resistance due to insertion, or a desired press-fit result.

5. A servo-controlled impacting device for orthopedic implants, the device comprising:

a controller configured to provide control signals to an impactor in response to feedback signals from at least one sensor proximate an orthopedic implant subject to a force applied by the impactor; and an interface coupled to the controller and configured to enable parameters to be set related to the operation of the controller;

wherein the impactor is pneumatically driven.

6. A servo-controlled impacting device for orthopedic implants, the device comprising:

a controller configured to provide control signals to an impactor in response to feedback signals from at least one sensor proximate an orthopedic implant subject to a force applied by the impactor; and an interface coupled to the controller and configured to enable parameters to be set related to the operation of the controller; wherein the controller determines control signals based on pre-programmed profiles and feedback signals from the at least one sensor.

7. A servo-controlled impacting device for orthopedic implants, the device comprising:

a controller configured to provide control signals to an impactor in response to feedback signals from at least one sensor proximate an orthopedic implant subject to a force applied by the impactor; and an interface coupled to the controller and configured to enable parameters to be set related to the operation of the controller; wherein the orthopedic implant comprises an osteochondral plug.

8. A surgical device comprising:

an orthopedic implant impactor configured to impact an orthopedic implant with sufficient force to insert the orthopedic implant; and a controller that communicates control signals to the orthopedic implant impactor, wherein the control signals are based on pre-programmed data and feedback signals received from one or more sensors.

9. The device of claim 8, wherein the control signals correspond to input parameters, the input parameters comprising implant shape, bone condition, resistance, and desired press-fit result.

10. The device of claim 8, wherein the controller is programmed to control the orthopedic implant impactor's frequency.

11. The device of claim 8, wherein the feedback signals are of a acoustic nature.

12. The device of claim 8, where one of the one or more sensors is coupled to the orthopedic implant impactor.

13. An impacting device for orthopedic implant surgery, the device comprising:

means for impacting an orthopedic implant to insert the orthopedic implant in a bone;

means for sensing conditions of the implanting;

means for determining control signals based on pre-programmed references and sensed conditions; and means for communicating the determined control signals to adjust force applied by the impacting means.

14. The device of claim 13, further comprising means for displaying orthopedic implant parameters and sensed conditions.

15. The device of claim 13, further comprising means for interfacing with the means for determining control signals.

16. The device of claim 13, wherein the pre-programmed references comprise implant parameters, bone parameters, and result parameters.

17. The device of claim 13, wherein the means for impacting an orthopedic implant is electrically driven.

18. A control device for use in osteochondral plug transplantation, the device comprising:

means for impacting a grafted osteochondral plug to insert the osteochondral plug into a pre-drilled hole;

means for sensing conditions of the impacting;

means for determining control signals based on sensed conditions; and means for communicating the determined control signals to adjust force applied by the impacting means.

* * * * *